United States Patent
Graham et al.

(10) Patent No.: US 7,892,399 B2
(45) Date of Patent: *Feb. 22, 2011

(54) LOCAL TENSION GENERATING AIR STABILIZATION SYSTEM FOR WEB PRODUCTS

(75) Inventors: Duck Graham, Vancouver (CA); Tamer Alev, Vancouver (CA); Michael Hughes, Vancouver (CA); Ron Beselt, Burnaby (CA); Glen Visser, North Vancouver (CA); Daniel Gordon, North Vancouver (CA); Salvatore Chirico, Port Moody (CA)

(73) Assignee: Honeywell ASCa Inc., Mississauga (CA)

( * ) Notice: Subject to any disclaimer, the term of this patent is extended or adjusted under 35 U.S.C. 154(b) by 317 days.

This patent is subject to a terminal disclaimer.

(21) Appl. No.: 12/129,461

(22) Filed: May 29, 2008

(65) Prior Publication Data

US 2009/0294084 A1    Dec. 3, 2009

(51) Int. Cl.
*D21F 1/36* (2006.01)
(52) U.S. Cl. .......... 162/193; 162/202; 34/114; 34/116
(58) Field of Classification Search .......... 162/193, 162/202, 263, 289, 297; 226/7, 97; 34/114, 34/116, 156, 160
See application file for complete search history.

(56) References Cited

U.S. PATENT DOCUMENTS

| 3,587,177 | A |   | 6/1971 | Overty |
| 4,252,512 | A |   | 2/1981 | Kornylak |
| 4,336,017 | A |   | 6/1982 | Desty |
| 4,601,116 | A |   | 7/1986 | Krimsky |
| 4,678,915 | A |   | 7/1987 | Dahlquist |
| 4,879,471 | A |   | 11/1989 | Dahlquist |
| 4,881,327 | A | * | 11/1989 | Hauser et al. .......... 34/114 |
| 4,932,140 | A | * | 6/1990 | Lepisto .......... 34/641 |
| 5,067,509 | A |   | 11/1991 | Hunter |
| 5,094,535 | A |   | 3/1992 | Dahlquist |

(Continued)

FOREIGN PATENT DOCUMENTS

WO    WO2005052248 A1    6/2005

OTHER PUBLICATIONS

Quadracci et al, Heat Transfer of an Inclined Coanda Jet to a Flexible Web, ASME Paper 94-WA/HT-21 (1994) New York, NY USA.

*Primary Examiner*—Mark Halpern
(74) *Attorney, Agent, or Firm*—Cascio Schmoyer & Zervas

(57) ABSTRACT

An air stabilization system employing two parallel, opposite-facing Coanda nozzles, with each nozzle exhausting gas at opposite directions, subjects a moving flexible web to opposing forces effective to create local tension within the web. Each nozzle includes an elongated slot that is perpendicular to the path of the moving web. The nozzles serve as separate points along the machine direction for controlling the height of the web. The operative surface with the nozzles can exhibit a flush surface. The nozzles can be formed on elevated structures on the operative surface. The operative surface can be covered with a transparent substrate to minimize shape distortions on the moving web and to prevent debris from collecting around the sensor. By modulating the velocities of gases exiting the nozzles, the shape of the web can be manipulated to present a planar contour. The air stabilization system can be incorporated into a caliper scanner.

19 Claims, 9 Drawing Sheets

U.S. PATENT DOCUMENTS

| | | |
|---|---|---|
| 5,166,748 A | 11/1992 | Dahlquist |
| 5,355,083 A | 10/1994 | George |
| 5,471,766 A * | 12/1995 | Heikkila et al. ............... 34/461 |
| 5,829,166 A * | 11/1998 | Klas ........................... 34/641 |
| 6,174,414 B1 | 1/2001 | Theriault |
| 6,193,810 B1 | 2/2001 | Baum |
| 6,210,534 B1 | 4/2001 | Graf |
| 6,281,679 B1 | 8/2001 | King |
| 6,543,765 B2 * | 4/2003 | Kerpe et al. .................. 271/195 |
| 6,743,338 B2 | 6/2004 | Ojala et al. |
| 6,899,792 B2 | 5/2005 | Hallberg |
| 6,936,137 B2 * | 8/2005 | Moeller et al. ............... 162/193 |
| 6,967,726 B2 | 11/2005 | King |
| 7,528,400 B2 * | 5/2009 | Duck et al. ............ 250/559.23 |
| 2007/0145307 A1 * | 6/2007 | Duck et al. ............ 250/559.01 |

\* cited by examiner

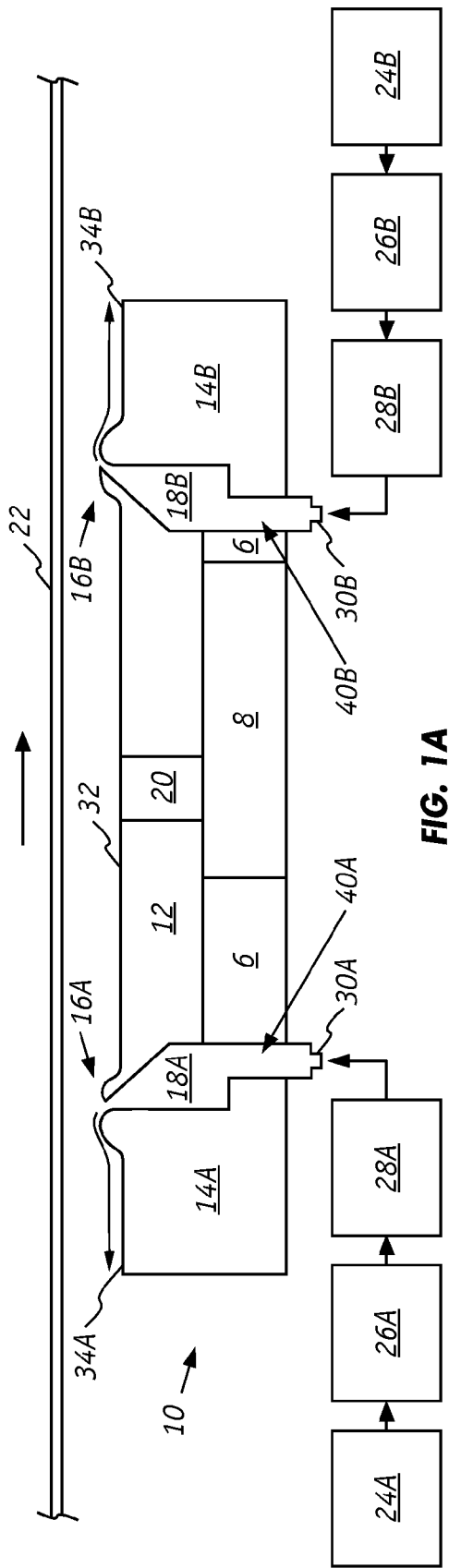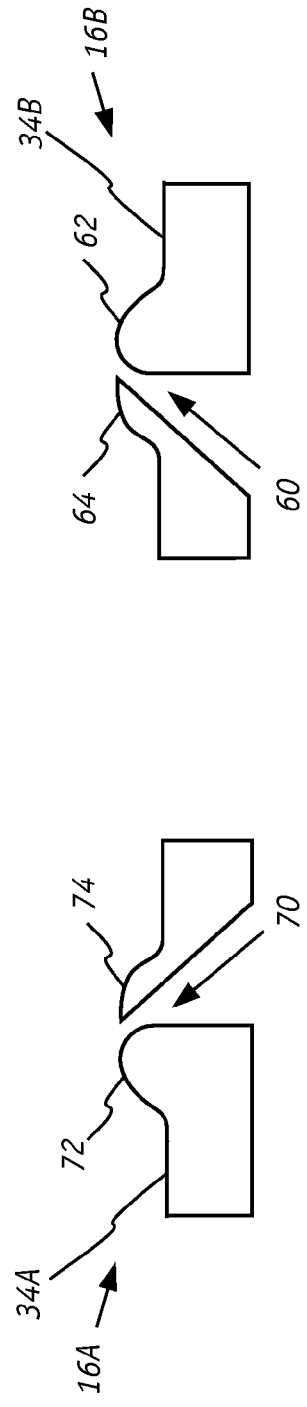

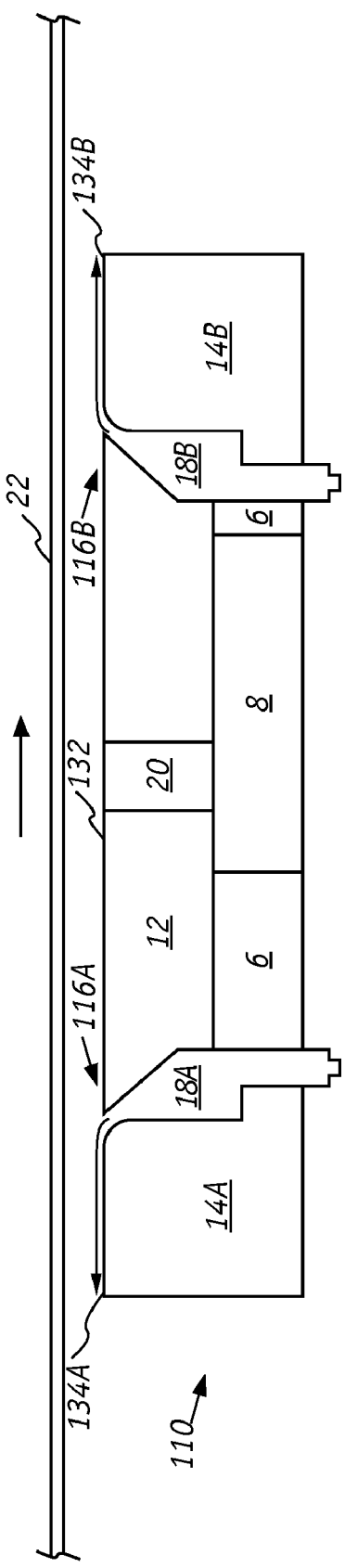
FIG. 6A
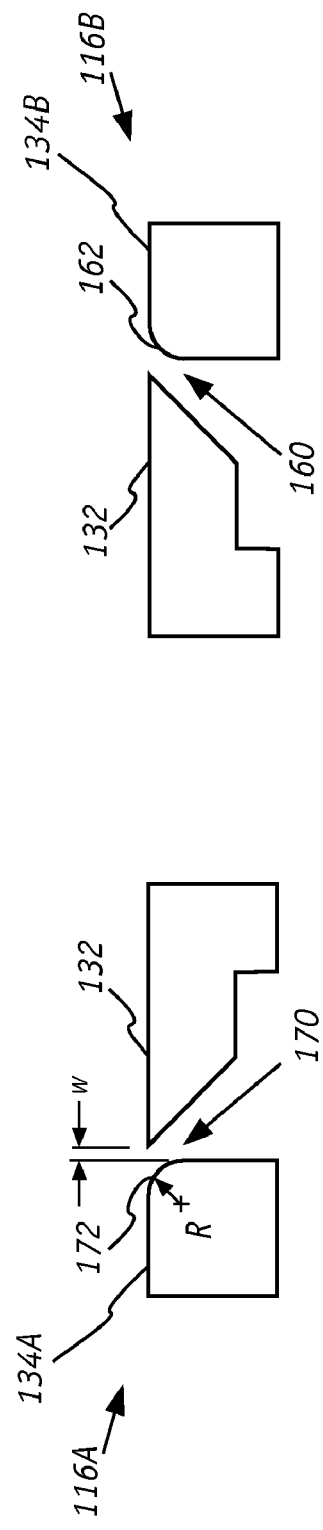
FIG. 6C
FIG. 6B

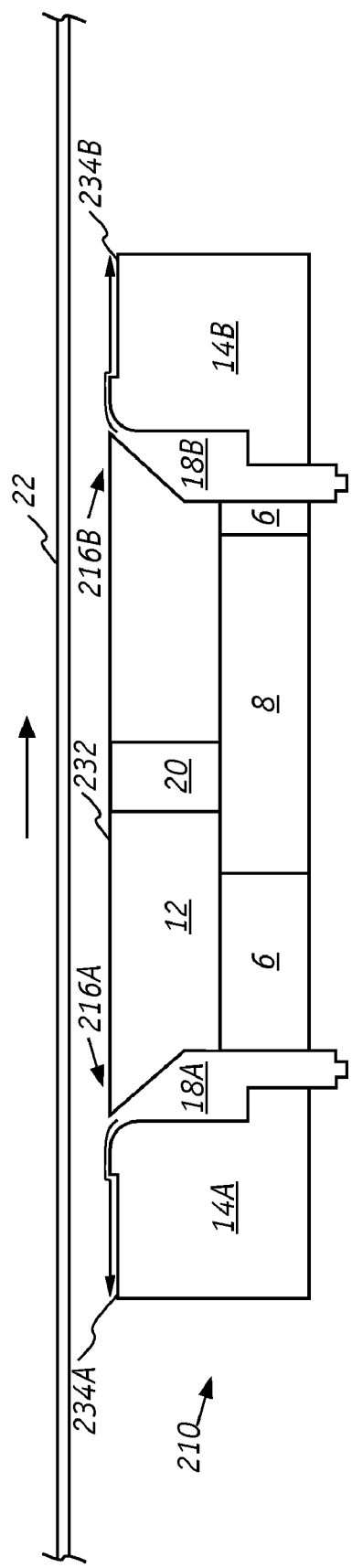
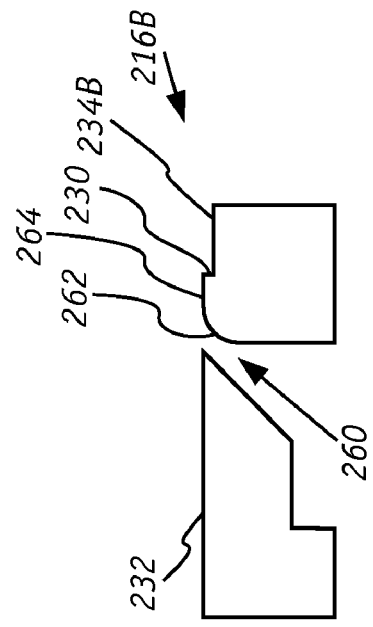
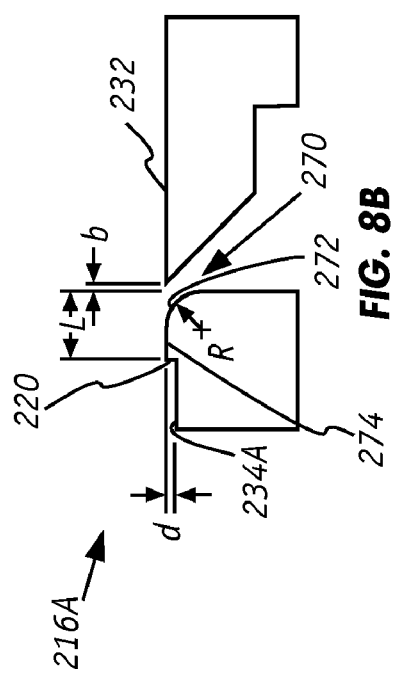

LOCAL TENSION GENERATING AIR STABILIZATION SYSTEM FOR WEB PRODUCTS

FIELD OF THE INVENTION

The present invention relates generally to an air stabilizer device for non-contacting support of a moving flexible continuous web of material. The air stabilizer employs two opposite-facing nozzles that direct jets of gas onto the moving web thereby imparting tension in the web. By regulating the speeds of the two jets of gas that are exhausted from the opposite-facing nozzles, the profile of the web as it passes over the air stabilizer can be controlled.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper.

It is well known to continuously measure certain properties of the paper material in order to monitor the quality of the finished product. These on-line measurements often include basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge. It is conventional to measure the caliper of sheet material upon its leaving the main dryer section or at the take-up reel with scanning sensors, as described, for example, in U.S. Pat. No. 6,967,726 to King et al. and U.S. Pat. No. 4,678,915 to Dahlquist et al.

In order to precisely measure some of the paper's characteristics, it is essential that the fast moving sheet of paper be stabilized at the point of measurement to present a consistent profile since the accuracy of many measurement techniques requires that the web stay within certain limits of flatness, height variation and flutter. U.S. Pat. No. 6,743,338 to Graeffe et al. describes a web measurement device having a measurement head with a reference surface that includes a plurality of holes formed therein. The reference part is configured so that there is an open space or channel below the reference part. By generating a negative pressure in the open space, suction force is exerted on the web thereby supporting it against the reference surface substantially over the entire measuring area. With such contacting methods, debris and contaminants tend to build on the sensing elements and clog the holes in the reference surface which adversely affect the accuracy of the measuring device. Moreover, to avoid paper degradation, stabilization must be accomplished with minimal or no contact to the stabilizing device. This is critical at the high speed at which web material such as paper is manufactured.

U.S. Pat. No. 6,281,679 to King et al. describes a non-contact web thickness measurement system which has dual sensor heads each located on opposite sides of a moving web. The system includes a web stabilizer that is based on a vortex of moving air and includes a clamp plate that is mounted near the web, which is to be stabilized, and a circular air channel within the clamp plate that is coincident with its upper surface. When air is introduced into the circular air channel, a field of low pressure is created over the channel and the web is pulled toward this ring of low pressure. While these vortex-type air clamps do provide adequate air bearing support they also create a "sombrero-type" profile on the web material in the center of its effective region, thus they do not generate a sufficiently flat profile for measurements. In measuring paper thickness, it has been found that this stabilizer system does not produce a sufficiently planar sheet profile.

U.S. Pat. No. 6,936,137 to Moeller et al. describes a linear air clamp or stabilizer, for supporting a moving web, which employs a single Coanda nozzle in conjunction with a "back-step" which is a depression downstream from the nozzle. As the web moves downstream over the air stabilizer, a jet of gas is discharged from the nozzle in a downstream direction that is parallel to the movement of the web. With this stabilizer, a defined area of web material rides on an air bearing as the web passes over the air clamp surface where a thickness measurement device is positioned.

When employed in a papermaking machine, a non-contacting caliper sensor is particularly suited for measuring the thickness of the finished paper near the take-up reel. The heads of the sensor are positioned on a scanner system that generally includes a pair of horizontally extending guide tracks that span the width of the paper. The guide tracks are spaced apart vertically by a distance sufficient to allow clearance for paper to travel between the tracks. The upper head and lower head are each secured to a carriage that moves back-and-forth over paper as measurements are made. The upper head includes a device that measures the height between the upper head and the upper surface of the web and the lower head includes a device that measures the height between the lower head to the lower surface of the web.

The lower or upper head includes an air stabilizer to support the moving paper. Ideally, the interrogations spots of each laser triangulation device are directly above each other. Accurate and precise measurements are attained when the two heads are in alignment but scanner heads will deviate from perfect alignment over time. A caliper sensor with misaligned sensor heads will not accurately measure a sheet that is not flat and current air stabilizers do not adequately support the moving sheet to present a sufficiently flat profile for measurement.

SUMMARY OF THE INVENTION

The present invention is based in part on the development of an air stabilization system that subjects a moving flexible web, which is traveling in the machine direction, to opposing forces sufficient to create local tension within the web. This can be achieved by employing two parallel, opposite-facing elongated Coanda nozzles positioned above or below the moving web with each nozzle exhausting gas at opposite directions. Each nozzle includes an elongated slot that is perpendicular to the path of the moving web. The locations of the two Coanda nozzles serve as separate positions on the machine direction for controlling the height of the moving web. By regulating the speed or pressure of the jets exiting the nozzles, the contour of the web can be manipulated to exhibit a planar contour between the two Coanda nozzles to enable accurate thickness and other measurements. Moreover, the air stabilization system's clamping capacity can be improved by optimizing the air pressure of the two exhausting gases so as to establish the requisite pressure region after each nozzle.

In one aspect, the invention is directed to an air stabilization system for supporting a flexible continuous web that is moving in a downstream machine direction (MD) that includes:

(a) a body having an operative surface facing the web wherein the operative surface has a web entry end and a web exit end that is downstream from the web entry end;

(b) a first nozzle, positioned on the operative surface at the web entry end, that defines a first slot that extends across the operative surface along a first direction that is substantially transverse to the MD and wherein a first elongated jet of pressurized gas is exhausted through the first slot and moves toward an upstream MD to impart a first controlled force on the web; and (c) a second nozzle, positioned on the operative surface at the web exit end, that defines a second slot that extends across the operative surface along a second direction that is substantially transverse to the MD, wherein a second elongated jet of pressurized gas is simultaneously exhausted through the second slot and moves toward a downstream MD to impart a second controlled force on the web and whereby the first force and the second force maintain at least a portion of the moving web, that is located between the web entry end and the web exit end, at a substantially fixed distance to the operative surface.

In a further aspect, the invention is directed to a method of supporting a flexible continuous web that is moving in a downstream machine direction (MD) along a path that includes the steps of:

(a) positioning an air stabilizer above or below the flexible continuous web along the path wherein the stabilizer includes:

(i) a body having an operative surface facing the web wherein the operative face has a web entry end and a web exit end that is downstream from the web entry end;

(ii) a first nozzle, positioned on the operative surface at the web entry end, that defines a first slot that extends across the operative surface along a first direction that is substantially transverse to the MD, wherein the first nozzle is fluid communication with a source of gas; and (iii) a second nozzle, positioned on the operative surface at the web exit end, that defines a second slot that extends across the operative surface along a second direction that is substantially transverse to the MD wherein the second nozzle is fluid communication with a source of gas;

(b) directing a first jet of gas from the first slot toward an upstream MD to impart a first force on the continuous web; and (c) simultaneously directing a second jet of gas from the second slot toward a downstream MD to impart a second force on the continuous web, whereby the first force and the second force maintain at least a portion of the moving web, that is located between the web entry end and the web exit end, at a substantially fixed distance to the operative surface.

In yet another aspect, the invention is directed to a system for monitoring a flexible continuous web that is moving in a downstream machine direction (MD) that includes:

(a) an air stabilization system for supporting the flexible continuous web, which has a first surface and a second surface, that includes:

(i) a body having an operative surface facing the web wherein the operative face has a web entry end and a web exit end that is downstream from the web entry end;

(ii) a first nozzle, positioned on the operative surface at the web entry end, that defines a first slot that extends across the operative surface along a first direction that is substantially transverse to the MD and wherein a first elongated jet of pressurized gas is exhausted through the first slot and moves toward an upstream MD to impart a first controlled force on the web; and (iii) a second nozzle, positioned on the operative surface at the web exit end, that defines a second slot that extends across the operative surface along a second direction that is substantially transverse to the MD, wherein a second elongated jet of pressurized gas is simultaneously exhausted through the second slot and moves toward a downstream machine direction to impart a second controlled force on the web and whereby the first force and the second force maintain at least a portion of the moving web, that is located between the web entry end and the web exit end, at a substantially fixed distance to the operative surface;

(b) a first sensor head that is disposed adjacent the first surface of the web; and (c) means for regulating the first jet of gas and the second jet of gas to control the web's profile along the process path over the operative surface.

BRIEF DESCRIPTION OF THE DRAWINGS

FIG. 1A is a cross sectional view of an embodiment of the air stabilizer system;

FIGS. 1B and 1C are enlarged cross sectional views of Coanda nozzles;

FIG. 6A is a cross sectional view of an embodiment of the air stabilizer system with a flush operative surface;

FIGS. 6B and 6C are enlarged cross sectional views of Coanda nozzles;

FIG. 8A is a cross sectional view of an embodiment of the air stabilizer system with Coanda nozzles each with a backstep;

FIGS. 8B and 8C are enlarged cross sectional views of Coanda nozzles;

DESCRIPTION PREFERRED EMBODIMENTS

Figure 2A:
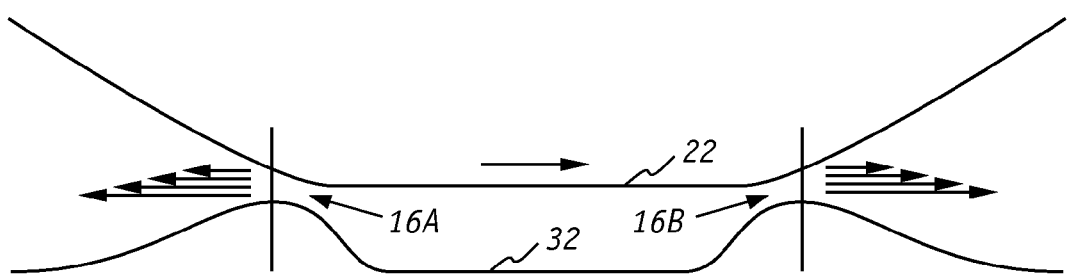
FIG. 2A depicts the sheet profile as it travels over the two Coanda nozzles and FIG. 2B is a schematic depiction of the velocity profiles of the gas jets from the nozzles.

FIG. 1A illustrates an embodiment of the air stabilization system 10 that includes a stainless steel body that is segmented into a central region 12, lateral region 14A and lateral region 14B. Central region 12 has an operative surface 32 that is situated between Coanda nozzles 16A and 16B. Each nozzle is formed within a dome-shaped structure protruding from the base of the body so that the nozzles are elevated relative to operative surface 32. The dome structures preferably exhibit slope curvatures that extend along the length of the nozzles. In a preferred arrangement, the air stabilization system 10 is employed with a laser-triangulation caliper device (not shown) that is positioned underneath. The laser beam incident on moving web 22 and the reflected light both pass through optical channel or orifice 20 that is formed in central region 12. The body further includes a lower portion 6 which supports central region 12. Lower aperture 8 permits optical access between the caliper device and optical path channel 20.

The air stabilization system 10 is positioned underneath a web of material 22 which is moving from left to right relative to the system; this direction being referred to as the downstream machine direction (MD) and the opposite direction being the upstream machine direction. The cross direction (CD) is transverse to the MD. Upper lateral surfaces 34A and 34B are preferably coplanar with operative surface 32.

As further described herein, the contour of web 22 as it travels over operative surface 32 can be controlled with the air stabilization system. In a preferred application of the air stabilization system, the profile of web 22 is substantially planar. Furthermore, the vertical height between web 22 and operative surface 32 can be regulated by controlling the speed of the gases exhausting through Coanda nozzles 16A and 16B. The higher the speed of the gases, the greater the suction force generated by the nozzles that is applied to the web 22.

The body of air stabilization system 10 further defines a chamber 18A that serves as an opening for Coanda nozzle 16A and a chamber 18B that serves as an opening for Coanda nozzle 16B. Chamber 18A is connected to plenum chamber 40A which in turn is connected to a source of gas 24A via conduit 30A. The gas flow rate into plenum 40A can be regulated by conventional means including pressure controller 28A and flow regulator valve 26A. The length of chamber 40A, as measured along the cross direction, preferably matches that of Coanda nozzle 16A. Plenum 40A essentially serves as a reservoir in which high pressure gas equilibrates before being evenly distributed along the length of Coanda nozzle 16A via chamber 18A. Conduit 30A can include a single channel which connects the source of gas 24A to plenum 40A; alternatively a plurality of holes drilled into the lower surface of the body can be employed. The plurality of holes should be spaced apart along the cross direction of the body in order to distribute gas evenly into plenum 40A.

Similarly, chamber 18B is in gaseous communication with plenum chamber 40B which is connected to a source of gas 24B via conduit 30B. Gas flowing into plenum 40B is regulated by pressure controller 28B and flow regulator valve 26B. The configurations of chamber 40B and conduit 30B are preferably the same as those of chamber 40A and conduit 30B, respectively.

Any suitable gas can be employed in gas sources 24A and 24B including for example, air, helium, argon, carbon dioxide. For most applications, the amount of gas employed is that which is sufficient to discharge the gas through the Coanda nozzles at a velocity of about 20 m/s to about 400 m/s. By regulating the velocities of the gaseous jets exiting Coanda nozzles 16A, 16B, the distance that moving web 22 is maintained above operative surface 32 can be adjusted. The air stabilization system can be employed to support a variety of flexible web products including paper, plastic, and the like. For paper that is continuously manufactured in large scale commercial papermaking machines, the web can travels at speeds of 200 m/min to 1800 m/min or higher. In operation, the air stabilization system preferably maintains paper web 22 at a distance ranging from about 100 µm to about 1000 µm above Coanda nozzles 16A and 16B.

As illustrated in FIG. 1B, Coanda nozzle 16A has a nozzle opening 70 that is formed on a protruding structure having an upstream upper surface 72 and a downstream upper surface 74. Upstream surface 72 is configured as an arcuately curved inner surface at nozzle opening 70 whereas downstream surface 74 presents a generally angled planar inner surface at nozzle opening 70. Gas emerging from nozzle opening 70 by virtue of the Coanda effect tends to follow a path along the curve of surface portion 72 and to travel upstream from right to left along upper lateral surface 34A. In the process, the surrounding gas is entrained in the air-flow emerging from nozzle opening 70.

Similarly, as illustrated in FIG. 1C, Coanda nozzle 16B with nozzle opening 60 is formed on a protruding structure having a downstream upper surface 62 and an upstream upper surface 64. Downstream surface 62 is configured as an arcuately curved inner surface at nozzle opening 60 while upstream surface 64 presents a generally angled planar inner surface at nozzle opening 60. Gas emerging from nozzle opening 60 follows the curve of surface portion 62 and travel downstream from left to right and along upper lateral surface 34B. Surrounding gas is entrained in the air-flow emerging from nozzle opening 60 to create a suction force.

FIG. 2A shows a side view of a sheet 22 as it passes over Coanda nozzles 16A and 16B, with each nozzle exhausting a jet of gas in opposite directions. The nozzles are set apart sufficiently to define a planar surface 32 between them. The sheet motion opposes the force imparted by upstream Coanda nozzle 16A, located at the web entry end, while the sheet motion is parallel to the force imparted by downstream Coanda nozzle 16B, located at the web exit end. The simultaneous opposing forces apply a tension on the moving sheet that creates the desired sheet profile between the nozzles as the sheet passes over the operative surface. The higher the air velocities from the dual nozzles, the greater the clamping force generated. With the air stabilization system, by increasing or decreasing the clamping force from the dual nozzles, the distance between moving web 22 and surface 32 can be correspondingly decreased or increased.

While the height of downstream Coanda nozzle 16B, as measured from the operative surface to the nozzle, is typically the same as that of upstream Coanda nozzle 16A, their heights can be different. By maintaining a height differential, the sheet profile between the nozzles can be modified. Preferably, the height of each Coanda nozzles ranges from 0.5 to 2.5 mm.

Figure 2B:

FIG. 2B shows the corresponding velocity profiles of the jets of gas exiting the Coanda nozzles. For illustrative purposes, the sheet is moving at a slow speed relative to the speed of the gases exiting the nozzles. For Coanda nozzle 16A, the gas exits in the upstream direction and curve 1 depicts the gas velocity (V) profile along a vertical path or height (H)

between Coanda nozzle 16A toward the sheet which is moving in the machine direction. The gas velocity decreases gradually and reverses direction at a position near the sheet. The gas velocity matches that of the web at the web's surface. For Coanda nozzle 16B wherein the gas exits in the downstream direction, curve 11 shows a gradual decrease in velocity from the nozzle to the moving web. In the case where the sheet velocity is negligible, the aerodynamics should be symmetric as the sheet is being essentially supported by the air clamping characteristics of the two nozzles.

Figure 3:
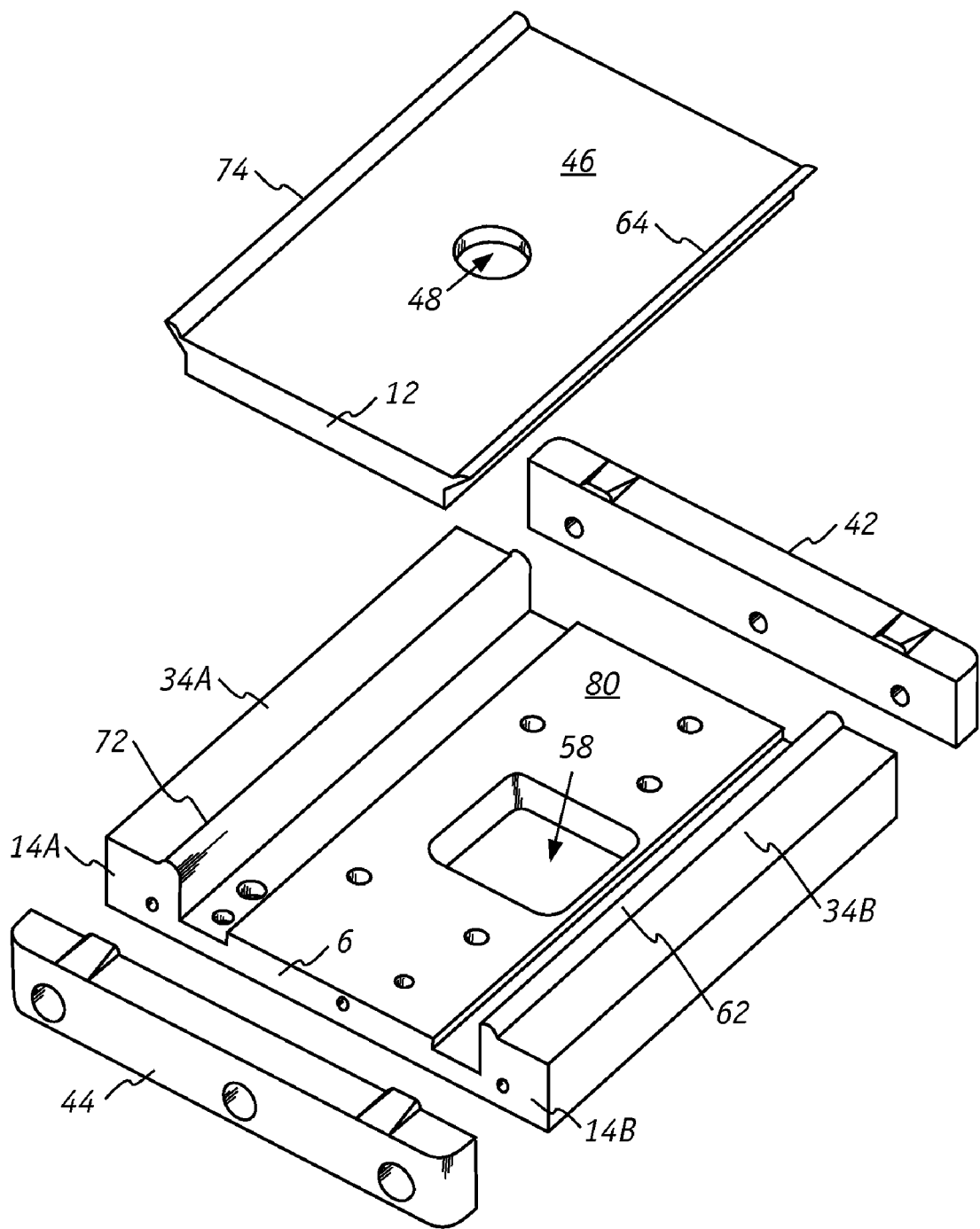
FIG. 3 is a perspective view of the air stabilizer system in dissembled form.

As shown in FIG. 3, the air stabilizing system can be constructed from four basic units that include a central body member 80, upper body member 46, and side supports 42, 44. They are attached together by conventional means including dowels and screws. The generally rectangular-shaped upper body member 46 has outer perimeters, at opposite ends, that define downstream upper surface 74 and upstream surface 64. A central region 12 has a measurement orifice 48 that serves as an optical path channel for a laser triangulation caliper device. Central body member 80 includes a middle portion 6 and lateral portions 14A and 14B and defines an opening 58 for access to the mounted device within orifice 20. The inward facing edge of lateral portion 14A defines upstream upper surface 72 and the inward facing edge of lateral portion 14B defines downstream upper surface 62. The air stabilizing system is formed by securing upper body member 46 onto central body member 80 so that the upper lateral surfaces 34A and 34B are coplanar with the surface of upper body member 46. Side supports 42 and 44 seal the internal plenums and chambers.

The air stabilization system can be incorporated into on-line dual head scanning sensor systems for papermaking machines which are disclosed in U.S. Pat. Nos. 4,879,471 to Dahlquist, 5,094,535 to Dahlquist et al., and 5,166,748 to Dahlquist, all of which are incorporated herein by reference. The width of the paper in the papermaking machines generally ranges from 5 to 12 meters and typically is about 9 meters. The dual heads, which are designed for synchronized movement, consist of an upper head positioned above the sheet and a lower head positioned below the sheet. The air stabilization system, which is preferably mounted on the lower head, clamps the moving paper to cause it to exhibit an essentially flat sheet profile for measurement as the upper and lower heads travel back and forth in the cross direction over the width of the paper.

Figure 4:
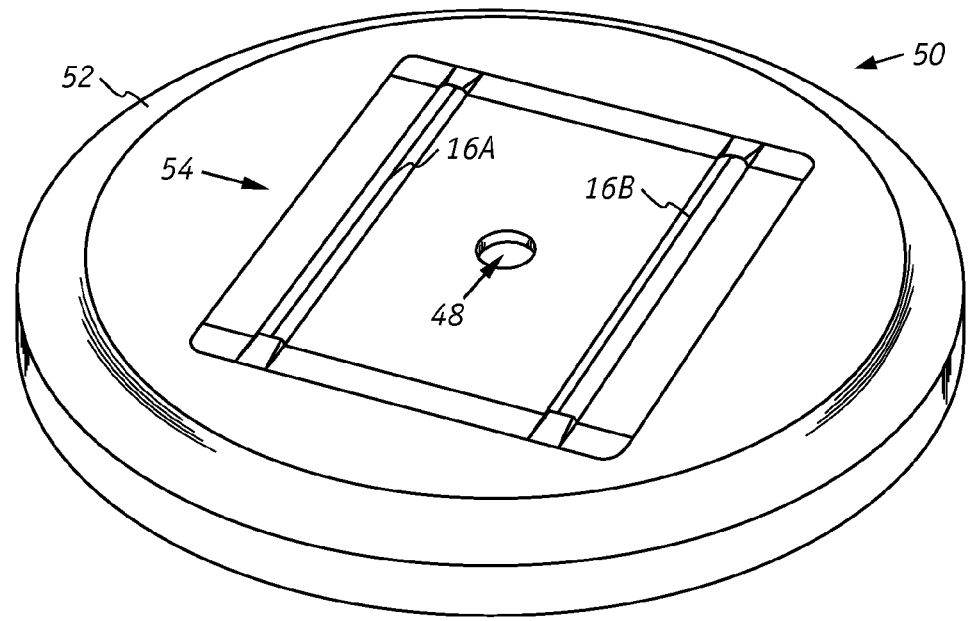
FIG. 4 shows the air stabilizer system as part of a sensor head.

FIG. 4 shows an air stabilization system that is incorporated into a recess compartment within substrate 52 that is part of lower head 50 of a scanning sensor. Measurement orifice 48 is situated between Coanda nozzles 16A and 16B. Substrate 52 is positioned so that a web product travels over the air stabilization system in machine direction 54 which is traverse to the lengths of the elongated Coanda nozzles. In operation, substrate 52 scans back and forth along the cross direction to generate measurements of the paper along the cross direction. When employed for measuring the caliper of paper, in one embodiment, the distance between nozzles 16A and 16B is about 75 mm and the length of each nozzle along the cross direction is about 50 mm.

Non-contacting caliper sensors such as those disclosed in U.S. Pat. No. 6,281,679 to King et al., which is incorporated herein by reference, include upper and lower heads equipped with laser triangulation devices. The caliper of a moving sheet that travels between the two heads is determined by identifying the positions of the upper and lower surfaces of the sheet with the laser triangulation devices and subtracting the results from a measure of the separation between the upper and lower heads.

Figure 5:
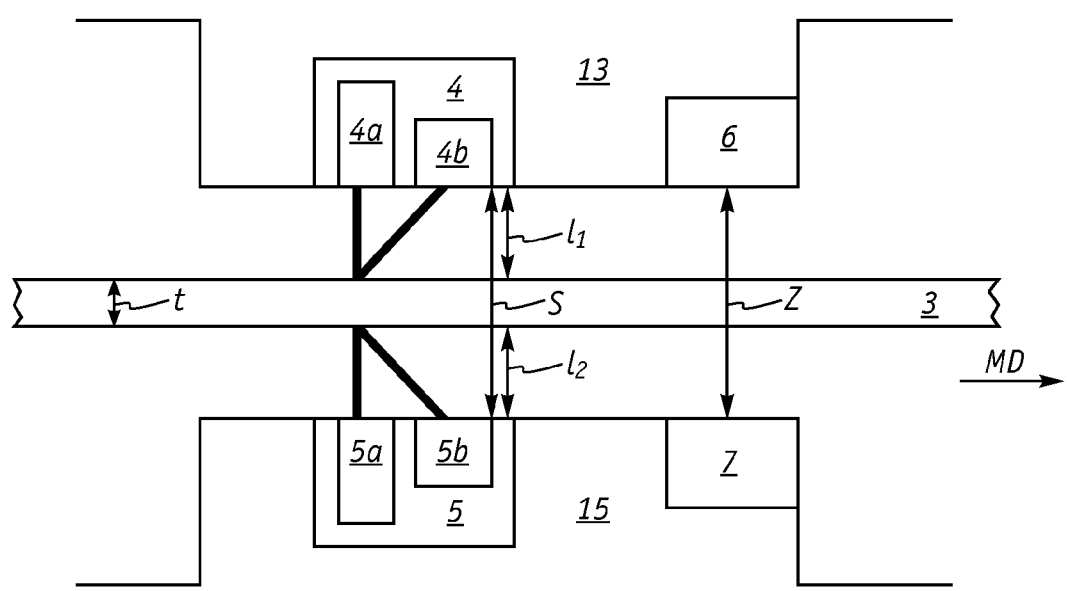
FIG. 5 is a cross sectional schematic view of a caliper measurement device.

FIG. 5 illustrates a representative non-contacting caliper sensor system that includes first and second scanner heads 13 and 15 respectively, which contain various sensor devices for measuring qualities, characteristics, or features of a moving web of material identified as 3. Heads 13 and 15 lie on opposite sides of web or sheet 3, and, if the measurement is to be performed in a scanning manner across the web in the cross direction, the heads are aligned to travel directly across from each other as they traverse the moving web which is moving in the machine direction. A first source/detector 4 is located in first head 13. A second source/detector 5 is located in second head 15. Source/detectors 4 and 5 comprise closely-spaced first and second sources 4a and 5a, respectively, and first and second detectors 4b and 5b, respectively, arranged so that measurement energy from first source 4a and interacting with a first surface of web 3 will return, at least in part to first detector 4b, and measurement energy from second source 5a and interacting with the opposite, or second surface, of web 3 will return, at least in part to second detector 5b.

The source and detector preferably comprise a laser triangulation source and detector, collectively being referred to as an interrogation laser. The source/detector arrangement is referred to generally as a distance determining means. From the measured path length from the source to the detector, values for the distance between each distance determining means and a measurement or interrogation spot on one of the web surfaces may be determined. The heads 13 and 15 are typically fixed in the position so that the interrogations spots do not move in the machine direction even as the heads are scanned in the cross direction.

For first distance determining means 4, the detected distance value between the distance determining means and a first measurement spot on the web surface (referred to as $l_1$) and for second distance determining means 5, the detected distance value between the distance determining means and a second measurement spot on the opposite web surface (referred to as $l_2$). For accurate thickness determinations, the first and second measurement spots (or interrogation spots) are preferably at the same point in the x-y plane, but on opposite sides of the web, i.e. the measurement spots will be separated by the web thickness. In an ideal static situation, the separation, s, between first and second distance determining means 4 and 5 would be fixed, resulting in a calculated value for web thickness, t, of: $t=s-(l_1+l_2)$. In practice, separation s can vary. To correct for this inconstancy in the separation s, a dynamic measurement of the spacing between the scanning heads is provided by a z-sensor means, which measures a distance z, between a z-sensor source/detector 6, located in the first head 13, and a z-sensor reference 7, located in the second head 15.

Because the scanner heads do not retain perfect mutual alignment as a sheet scans between them, the air stabilization system of the present invention is employed with either the lower head, upper head, or both heads to keep the sheet flat so that small head misalignments do not translate into erroneous caliper readings, i.e., caliper error due to head misalignment and sheet angle.

FIG. 6A illustrates an embodiment of the air stabilization system 110 with a smooth, flush operative surface, supporting moving web 22. The stabilizer includes a body that is segmented into a central region 12, lateral region 14A and lateral region 14B. Central region 12 has an operative surface 132 that is situated between Coanda nozzles 116A and 116B, which are in gaseous communication with chambers 18A and 18B, respectively. Coanda nozzles 116A and 116B exhaust jets of gas in opposite directions. Independently regulated sources of pressurized gas, which are described above for the air stabilization system 10 of FIG. 1A, can be employed and are connected to chamber 18A and 18B. Central region 12 defines an optical channel 20 whose upper surface is flush with operative surface 132 and is part of the operative surface 132. The body further includes a lower portion 6 which supports central region 12. Aperture 8 permits access to optical channel 20. Upper lateral surfaces 134A and 134B are preferably coplanar with operative surface 132 to define a smooth flush surface over the body.

As illustrated in FIG. 6B, Coanda nozzle 116A has a Coanda slot 170 between upper surface 134A and operative surface 132. Coanda slot 170 has a curved convex surface 172 on its downstream side. Preferably this surface has a radius of curvature (R) ranging from about 1.0 mm to about 10 mm. Gas flow from Coanda slot 170 follows the downstream trajectory of curved surface 172, so as to flow in the upstream MD relative to the moving web. Preferably, slot 170 has a width (w) of about 3 mils (76 μm) to 5 about mils (127 μm). The air clamp's suction force draws the web closer to the stabilizer as the web approaches the stabilizer. However, the web should not be permitted to get too close to the nozzles as this would actually cut off gas flow from the nozzles. This would cause the local pressure to rise and the increase force would push to web away from the stabilizer.

Similarly, as shown in FIG. 6C, Coanda nozzle 116B has a Coanda slot 160 between upper surface 134B and operative surface 132. Coanda slot 160 has a curved convex surface 162 on its downstream side. Gas flow from the Coanda slot 160 follows the downstream trajectory of curved surface 162 so as to flow in the downstream MD. The dimensions of Coanda nozzle 116B can be the same as those of Coanda nozzle 116A.

A stainless steel air clamp stabilizer having the configuration shown in FIGS. 6A, 6B and 6C was incorporated into a laser triangulation scanning sensor. Each of the two Coanda nozzles had a slot having a width (w) of 0.1 mm and a curvature radius (R) of 1.5 mm. The nozzles were approximately 43 mm apart as measured from the center of each nozzle slot. The air clamp was employed to support a moving web of paper that was traveling at about 1500 m/min and had a basis weight of 45 grams per square meter (gsm). The term "basis weight" refers to the mass or weight per unit area of the paper. The distance between the upper surface of the paper and the center of the operative surface of the air stabilizer was measured as the sensor was scanned across the 8.5 m sheet with a laser triangulation sensor as the paper sheet moved horizontally over the surface of the air clamp stabilizer.

Figure 7A:
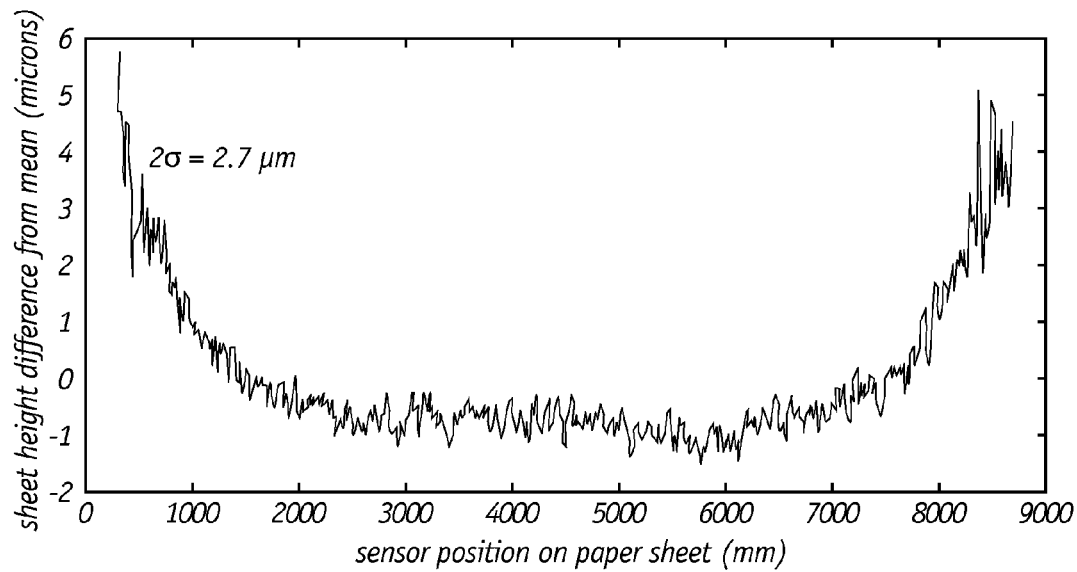
FIG. 7A is a graph of height of sheet around the mean height vs. scanner displacement.
Figure 7B:
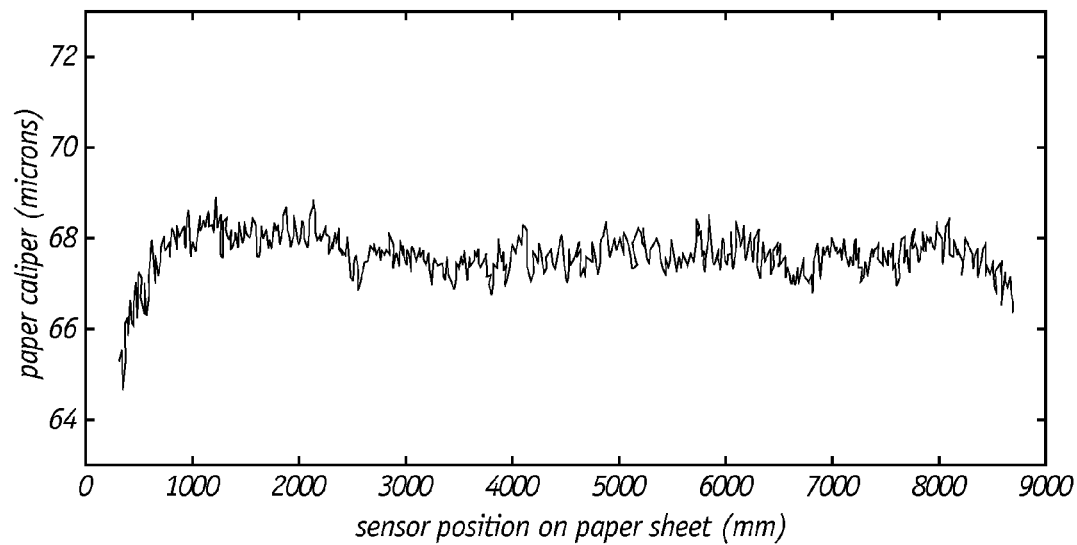
FIG. 7B is a graph of caliper profile vs. scanner displacement.

FIG. 7A depicts the height of the sheet around the mean distance vs. the scanner displacement or position in the cross direction of the moving sheet. The curve shows that the sheet contour is substantially flat; the 2-sigma variation in the sheet height is 2.7 microns. FIG. 7B depicts the corresponding laser caliper profile derived from 10 cross direction scans from one side of the paper to the other.

FIG. 8A illustrates an embodiment of the air stabilization system 210 that incorporates opposite-facing nozzles that are configured with backsteps that increase the suction force which is applied to moving web 22. The stabilizer includes a body that is segmented into a central region 12, lateral region 14A and lateral region 14B. Central region 12 has an operative surface 232 that is situated between Coanda nozzles 216A and 216B, which are in gaseous communication with chambers 18A and 18B, respectively. Coanda nozzles 216A and 216B exhaust jets of gas in opposite directions toward surface 234A and 234B, respectively, which are downstream of the backstep features of nozzles. Independently regulated sources of pressurized gas, which are described above for the air stabilization system 10 of FIG. 1A, can be employed and are connected to chamber 18A and 18B. Central region 12 includes an optical channel 20. The body further includes a lower portion 6 which supports central region 12. Aperture 8 permits access to optical channel 20.

As illustrated in FIG. 8B, Coanda nozzle 216A has a Coanda slot 270 between upper surface 274 and operative surface 232 which are preferably coplanar. Coanda slot 270 has a curved convex surface 272 on its downstream side. Preferably this surface has a radius of curvature (R) ranging from about 1.0 mm to about 10 mm, and in one embodiment it is about 1.6 mm. Airflow from the Coanda slot 270 follows the trajectory of the curved surface 272. The term "backstep" is meant to encompass a depression on the stabilizer surface located a distance downstream from Coanda slot 270 preferably sufficient to create a vortex. The combination of the Coanda slot and backstep generates an amplified suction force and an extensive air bearing.

Specifically, backstep 220 allows a Coanda jet to expand and create an additional suction force. It should be noted that jet expansion is necessary to create the suction force but vortex formation is not a prerequisite. Indeed, vortex formation does not always occur downstream from the backstep and is not necessary for operation of the air clamp stabilizer. The stabilizer's suction force initially draws the web closer to the stabilizer as the web approaches the stabilizer. Subsequently, the air bearing supports and reshapes the web so that the web exhibits a relatively flat profile as it passes over the backstep. While backstep 220 is most preferably configured as a 90 degrees vertical wall, the backstep can exhibit a more gradual contour so that the upper and lower surfaces can be joined by a smooth, concavely curved surface. Preferably, Coanda slot 270 has a width (b) of about 3 mils (76 μm) to 5 about mils (127 μm). The distance (d) from the upper surface 274 to lower surface 234A, which are preferably parallel to each other, is preferably between about 100 to 1000 μm. Preferably the backstep location (L) is about 1 mm to about 6 mm and preferably about 2 mm to 3 from Coanda slot 270.

Similarly, as shown in FIG. 8C, Coanda nozzle 216B has a Coanda slot 260 between upper surface 264 and operative surface 232. Coanda slot 260 has a curved surface 262 on its downstream side. The dimensions of structures forming Coanda nozzle 216B, including backstep 230 and lower surface 234B, can be the same as those for Coanda nozzle 216A.

Figure 9:
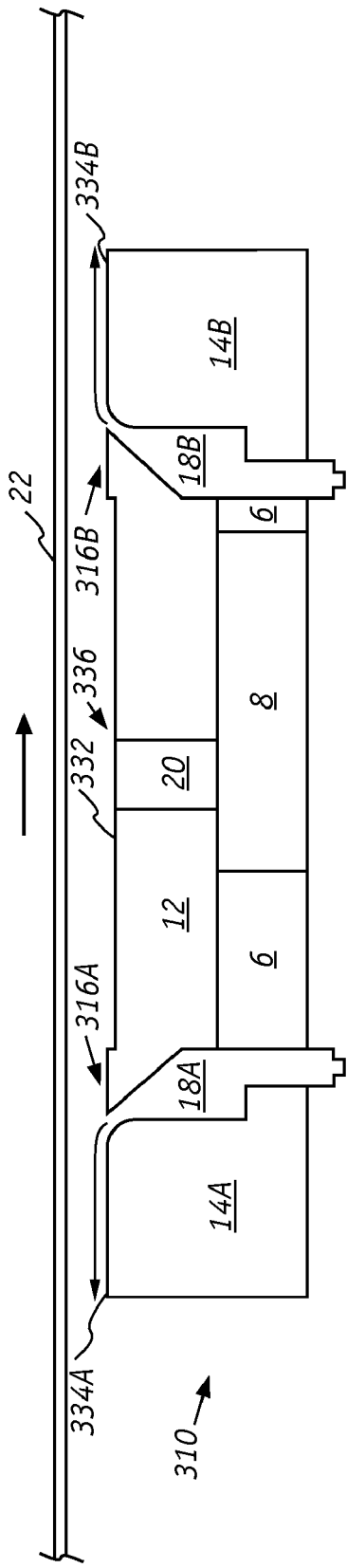
FIG. 9 is a cross sectional view of an embodiment of the air stabilizer system with a channel in the operative surface.

FIG. 9 illustrates an embodiment of air stabilization system 310 wherein the operative surface 332 is located on the lower surface of channel 336 that is formed in the body of the stabilizer. Thus, operative surface 332 is located farther away from moving web 22 to reduce the likelihood that web 22 comes into contact with operative surface 332. The stabilizer includes a body that is segmented into a central region 12, lateral region 14A, with upper surface 334A, and lateral region 14B, with upper surface 334B. Central region 12 has an optical operative surface 332 that is situated between opposite facing Coanda nozzles 316A and 316B, which are in gaseous communication with chambers 18A and 18B, respectively. Central region 12 defines an optical channel 20. The depth of channel 334 within central region 12 can range from 1400 μm to 2000 μm or more. The remaining structures of the stabilizer can be same as those illustrated in FIG. 6A; however, it is understood that a channel can be incorporated into any air stabilization system described above to provide additional clearance between the moving web and operative surface.

Figure 10:
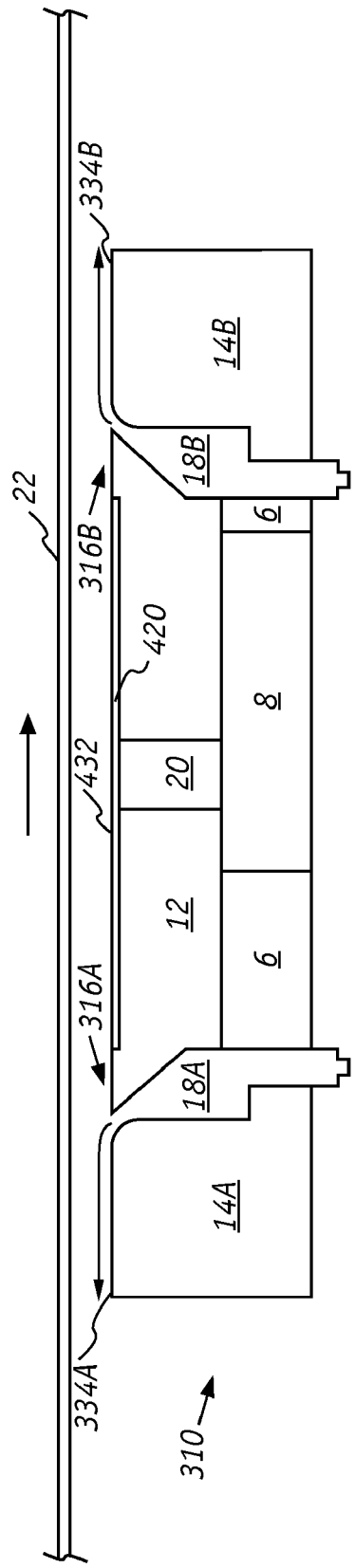
FIG. 10 is a cross sectional view of an embodiment of the air stabilizer with a transparent smooth substrate on the operative surface.

FIG. 10 illustrates the air stabilization system of FIG. 9 with a transparent substrate 420, such as glass, inserted within channel 334 in order to optical channel 20. Substrate 420 prevents debris from accumulating within optical channel 20 which can adversely affect sensor measurements and distort the web profile. Upper surface 432 of substrate 420, which presents a smooth surface, eliminates these potential problems. Transparent substrates can also be employed with any of the air stabilization systems described above. Upper surface 432 is preferably coplanar with upper surfaces 334A and 334B so that the surfaces of the stabilizer are flush.

Figure 11:
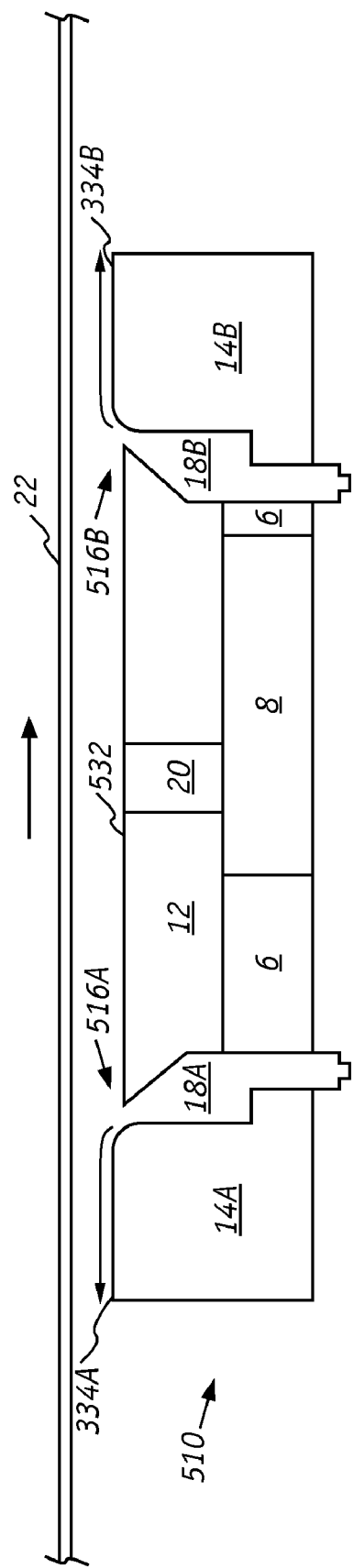
FIG. 11 is a cross sectional view of an embodiment of the air stabilizer with recess operative surface.

Finally, FIG. 11 illustrates an embodiment of air stabilization system 510 that includes a body that is segmented into a central region 12, lateral region 14A, with upper surface 334A, and lateral region 14B, with upper surface 334B. Upper surfaces 334A and 334B are preferably parallel and coplanar. Central region 12 is set back so that central operative surface 532 is farther away from moving web 22, than are upper surfaces 334A and 334B, to reduce the likelihood that web 22 comes into contact with operative surface 532. Central operative surface 532 is preferably about 0.025 in. (0.64 mm) to 0.011 in. (0.28 mm) lowered that the lateral operative surfaces formed by upper surfaces 334A and 334B. Opposite facing Coanda nozzles 516A and 516B, are in gaseous communication with chambers 18A and 18B, respectively. The remaining structures of the stabilizer can be same as those illustrated in FIG. 6A.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An air stabilization system for supporting a flexible continuous web that is moving in a downstream machine direction (MD) that comprises:
    (a) a body having an operative surface facing the web wherein the operative surface has a web entry end and a web exit end that is downstream from the web entry end wherein the operative surface is segmented into a central region, a first lateral region, and a second lateral region, which define coplanar surfaces that are substantially flush with each other;
    (b) a first nozzle, positioned on the operative surface at the web entry end and between the first lateral region and the central region, that defines a first slot that extends across the operative surface along a first direction that is substantially transverse to the MD wherein a first elongated jet of pressurized gas is exhausted through the first slot and moves toward an upstream MD to impart a first controlled force on the web wherein the first nozzle comprises a slot in the body that is in fluid communication with a first source of gas and has a first elongated opening at a first surface of the body wherein the first slot has a first curved convex surface at the first elongated opening on its upstream side and wherein the first elongated opening is disposed on a first elevation of the operative surface; and
    (c) a second nozzle, positioned on the operative surface at the web exit end and between the second lateral region and the central region, that defines a second slot that extends across the operative surface along a second direction that is substantially transverse to the MD, wherein a second elongated jet of pressurized gas is simultaneously exhausted through the second slot and moves toward a downstream MD to impart a second controlled force on the web wherein the second nozzle comprises a slot in the body that is in fluid communication with a second source of gas and has a second elongated opening at a second surface of the body wherein the second slot has a second curved convex surface at the second elongated opening on its downstream side and the second elongated opening is disposed on a second elevation of the operative surface and whereby the first force and the second force maintain at least a portion of the moving web, that is located between the web entry end and the web exit end, at a substantially fixed distance to the operative surface.

2. The system of claim 1 wherein the vertical distance between the operative surface and the first elongated opening is less than the vertical distance between the operative surface and the second elongated opening.

3. The system of claim 1 wherein the distance between the first elongated opening to the second elongated opening ranges from 5 to 100 mm.

4. The system of claim 1 comprising means for independently controlling the speed of the first elongated jet and the speed of the second elongated jet.

5. The system of claim 4 wherein the speed of the first elongated jet as it is exhausted from the first slot ranges from 20 to 400 m/s and the speed of the second elongated jet as it is exhausted from the second slot ranges from 20 to 400 m/s.

6. The system of claim 1 wherein the first slot has a length as measured along a cross direction that is transverse to MD that ranges from 25 to 125 mm and the second slot has a length as measured along a cross direction that ranges from 25 to 125 mM.

7. An air stabilization system for supporting a flexible continuous web that is moving in a downstream machine direction (MD) that comprises:
    (a) a body having an operative surface facing the web wherein the operative surface has a web entry end and a web exit end that is downstream from the web entry end wherein the operative surface is segmented into a central region, a first lateral region, and a second lateral region, wherein the three regions define coplanar surfaces that are substantially flush with each other;
    (b) a first nozzle, positioned on the operative surface at the web entry end and between the first lateral region and the central region, that defines a first slot that extends across the operative surface along a first direction that is substantially transverse to the MD wherein a first elongated jet of pressurized gas is exhausted through the first slot and moves toward an upstream MD to impart a first controlled force on the web wherein the first nozzle comprises a slot in the body that is in fluid communication with a first source of gas and has a first elongated opening at a first surface of the body wherein the first slot has a first curved convex surface at the first elongated opening on its upstream side and wherein the first elongated opening is disposed on a first lateral region surface which has a first upper portion; and
    (c) a second nozzle, positioned on the operative surface at the web exit end and between the second lateral region and the central region, that defines a second slot that extends across the operative surface along a second direction that is substantially transverse to the MD, wherein a second elongated jet of pressurized gas is simultaneously exhausted through the second slot and moves toward a downstream MD to impart a second controlled force on the web and wherein the second nozzle comprises a slot in the body that is in fluid communication with a second source of gas and has a second elongated opening at a second surface of the body wherein the second slot has a second curved convex surface at the second elongated opening on its downstream side and wherein the second elongated opening is disposed on a second lateral region surface which has a second upper portion and whereby the first force and the second force maintain at least a portion of the moving web, that is located between the web entry end and the web exit end, at a substantially fixed distance to the operative surface.

8. The system of claim 7 wherein the first lateral region surface has as a first lower portion that is upstream from the first upper portion wherein the first upper portion is vertically spaced from the first lower portion and wherein the second lateral region surface has a second lower portion that is downstream from the second upper portion and the second upper portion is vertically spaced from the second lower portion.

9. The system of claim 7 wherein the body has a channel, that is located between the web entry end and the web exit end, which has an upper surface that forms the operative surface.

10. The system of claim 9 wherein at least a portion of the channel is covered with a transparent substrate.

11. A system for monitoring a flexible continuous web that is moving in a downstream machine direction (MD) that comprises:
(a) an air stabilization system for supporting of the flexible continuous web, which has a first surface and a second surface, that comprises:
(i) a body having an operative surface facing the web wherein the operative face has a web entry end and a web exit end that is downstream from the web entry end wherein the operative surface is segmented into a central region, a first lateral region, and a second lateral region, which define coplanar surfaces that are substantially flush with each other;
(ii) a first nozzle, positioned on the operative surface at the web entry end and between the first lateral region and the central region, that defines a first slot that extends across the operative surface along a first direction that is transverse to the MD and wherein a first elongated jet of pressurized gas is exhausted through the first slot and moves toward an upstream MD to impart a first controlled force on the web wherein the first nozzle comprises a slot in the body that is in fluid communication with a first source of gas and has a first elongated opening at a first surface of the body wherein the first slot has a first curved convex surface at the first elongated opening on its upstream side and wherein the first elongated opening is disposed on a first elevation of the operative surface; and
(iii) a second nozzle, positioned on the operative surface at the web exit end and between the second lateral region and the central region, that defines a second slot that extends across the operative surface along a second direction that is transverse to the MD, wherein a second elongated jet of pressurized gas is simultaneously exhausted through the second slot and moves toward a downstream machine direction to impart a second controlled force on the web wherein the second nozzle comprises a slot in the body that is in fluid communication with a second source of gas and has a second elongated opening at a second surface of the body wherein the second slot has a second curved convex surface at the second elongated opening on its downstream side and the second elongated opening is disposed on a second elevation of the operative surface and whereby the first force and the second force maintain at least a portion of the moving web, that is located between the web entry end and the web exit end, at a substantially fixed distance to the operative surface;
(b) a first sensor head that is disposed adjacent the first surface of the web; and
(c) means for regulating the first jet of gas and the second jet of gas to control the web's profile along the process path over the operative surface.

12. The system of claim 11 wherein the first sensor head is disposed within the body such that an active surface of the first sensor head is flush with the operative surface and the system further comprising (d) a second sensor head that is disposed adjacent the second surface of the web.

13. The system of claim 12 wherein the first sensor includes means for measuring the distance between the first sensor and the first surface and the second sensor includes means for measuring the distance between the second sensor and the second surface and wherein the system further includes means for measuring the distance between the first sensor and the second sensor.

14. The system of claim 11 wherein the distance between the first elongated opening to the second elongated opening ranges from 5 to 100 mm.

15. The system of claim 11 comprising means for independently controlling the speed of the first elongated jet and the speed of the second elongated jet.

16. A system for monitoring a flexible continuous web that is moving in a downstream machine direction (MD) that comprises:
(a) an air stabilization system for supporting of the flexible continuous web, which has a first surface and a second surface, that comprises:
(i) a body having an operative surface facing the web wherein the operative face has a web entry end and a web exit end that is downstream from the web entry end wherein the operative surface is segmented into a central region, a first lateral region, and a second lateral region, which define coplanar surfaces that are substantially flush with each other;
(ii) a first nozzle, positioned on the operative surface at the web entry end and between the first lateral region and the central region, that defines a first slot that extends across the operative surface along a first direction that is transverse to the MD and wherein a first elongated jet of pressurized gas is exhausted through the first slot and moves toward an upstream MD to impart a first controlled force on the web wherein the first nozzle comprises a slot in the body that is in fluid communication with a first source of gas and has a first elongated opening at a first surface of the body wherein the first slot has a first curved convex surface at the first elongated opening on its upstream side and wherein the first elongated opening is disposed on a first lateral region surface which has a first upper portion; and
(iii) a second nozzle, positioned on the operative surface at the web exit end and between the second lateral region and the central region, that defines a second slot that extends across the operative surface along a second direction that is transverse to the MD, wherein a second elongated jet of pressurized gas is simultaneously exhausted through the second slot and moves toward a downstream machine direction to impart a second controlled force on the web wherein the second nozzle comprises a slot in the body that is in fluid communication with a second source of gas and has a second elongated opening at a second surface of the body wherein the second slot has a second curved convex surface at the second elongated opening on its downstream side and wherein the second elongated opening is disposed on a second lateral region surface which has a second upper portion and and whereby the first force and the second force maintain at least a portion of the moving web, that is located between the web entry end and the web exit end, at a substantially fixed distance to the operative surface;

(b) a first sensor head that is disposed adjacent the first surface of the web; and (c) means for regulating the first jet of gas and the second jet of gas to control the web's profile along the process path over the operative surface.

17. The system of claim 16 wherein the first lateral region surface has a first lower portion that is upstream from the first upper portion wherein first upper portion is vertically spaced from the first lower portion and wherein the second lateral region surface has a second lower portion that is downstream from the second upper portion wherein the second upper portion is vertically spaced from the second lower portion.

18. The system of claim 16 wherein the body has a channel, that is located between the web entry end and the web exit end, which has an upper surface that forms the operative surface.

19. The system of claim 18 wherein at least a portion of the channel is covered with a transparent substrate.

* * * * *